United States Patent [19]

Wandrey et al.

[11] Patent Number: 5,200,326
[45] Date of Patent: Apr. 6, 1993

[54] METHOD FOR THE FERMENTATIVE PRODUCTION OF L-AMINO ACIDS FROM α-KETO ACIDS

[75] Inventors: Christian Wandrey; Rolf Wichmann, both of Jülich; Ulrich Groeger; Manfred Kircher, both of Bielefeld; Wolfgang Leuchtenberger, Bruchkobel; Eberhard Breuker, Detmold, all of Fed. Rep. of Germany

[73] Assignee: Degussa AG, Fed. Rep. of Germany

[21] Appl. No.: 44,678

[22] Filed: May 1, 1987

[30] Foreign Application Priority Data

May 2, 1986 [DE] Fed. Rep. of Germany ....... 3614586

[51] Int. Cl.$^5$ .................. C12P 13/04; C12P 13/06
[52] U.S. Cl. ................................ 435/106; 435/116; 435/840; 435/843
[58] Field of Search ............... 435/116, 106, 110, 840, 435/818, 253.6, 107, 108, 109, 111, 112, 113, 114, 115

[56] References Cited

U.S. PATENT DOCUMENTS

3,959,075  5/1976  Inuzuka et al. .................... 435/115

FOREIGN PATENT DOCUMENTS

3419585  11/1985  Fed. Rep. of Germany ...... 435/116
2147579  5/1985  United Kingdom .

OTHER PUBLICATIONS

Lehninger, A. 1975. *Biochemistry*-Worth Publishers, Inc., New York, pp. 700, 704.
Kinoshita, S. 1985, "Glutamic Acid Bacteria", Inc. In: *Biology of Industrial Microorganisms*, Demain, A. L. et al., The Benjamin/Cummings Publishing Co., Menlo Park, Calif. p. 127.
Metzler, D. E. 1977, *Biochemistry*, Academic Press, New York p. 547.
Akasahi et al. "Effect of Oxygen Supply on L-Lysine, L-Threonine, and L-Isoleucine Fermentations," Agric. Biol. Chem., 1979, vol. 43 No. 10, pp. 2087-2092.
Reed, G. 1982, *Prescott & Dunn's Industrial Microbiology*, 4th Edition, AVI Publishing Co., Inc., Westport, Conn. pp. 846-847.
Sikyta, B 1984, *Methods in Industrial Microbiology*, John Wiley & Sons, pp. 64-69.
Holst, O. et al. 1985, *Applied Microbiology and Biotechnology*, vol. 23, pp. 10-14.
Tangnu, S. K. et al. 1981 *Process Biochemistry*, Dec./-Jan. 1980/81, pp. 22-43.

Primary Examiner—Richard A. Schwartz
Assistant Examiner—Mary E. Mosher
Attorney, Agent, or Firm—Cushman, Darby & Cushman

[57] ABSTRACT

The invention is directed to a method of producing L-amino acids from α-ketocarboxylic acids by means of continuous fermentation with the aid of glutamate producing bacteria with biomass retention in which the cells are separated by microfiltration and/or centrifugal separators.

14 Claims, 1 Drawing Sheet

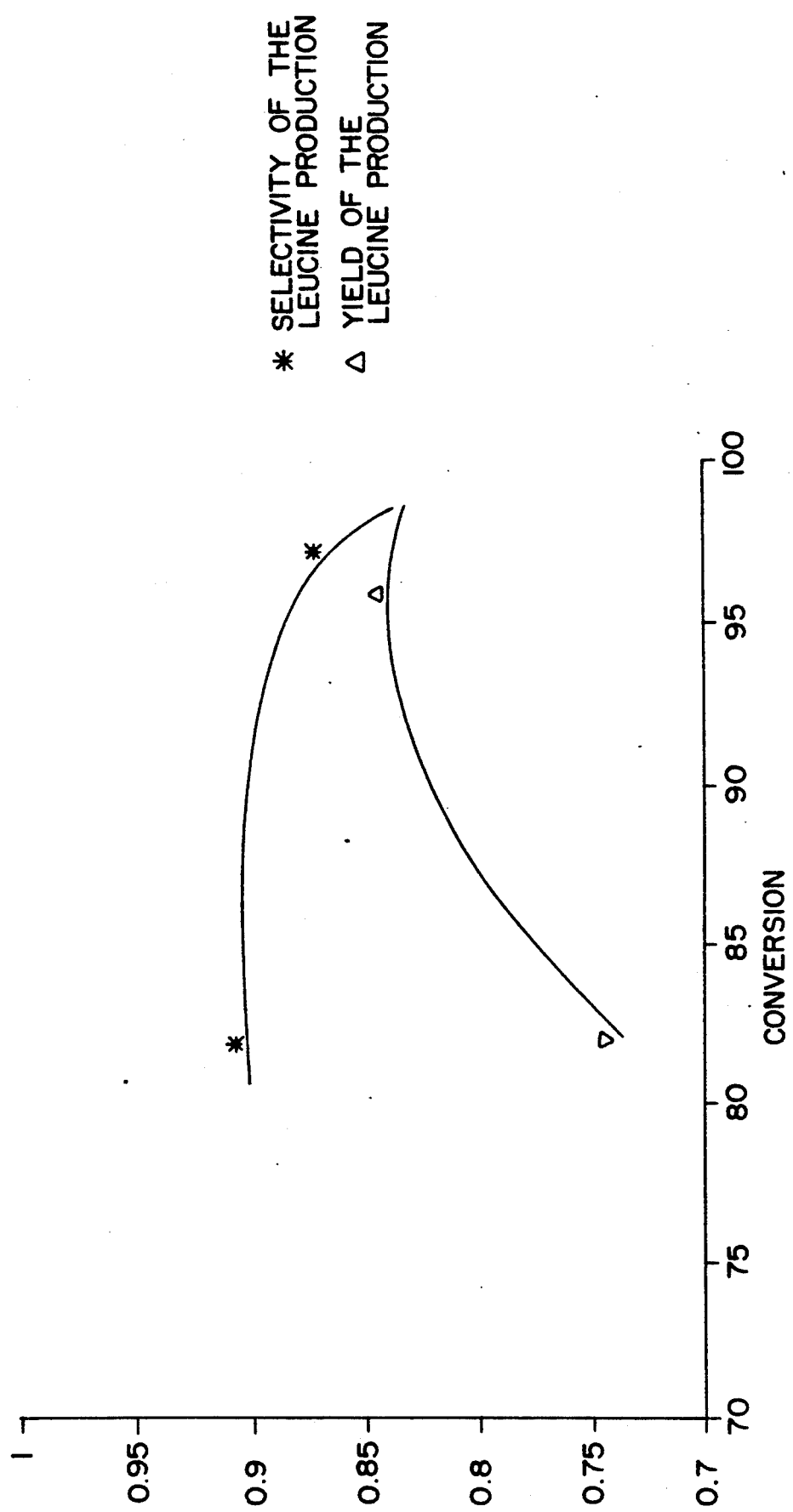

METHOD FOR THE FERMENTATIVE PRODUCTION OF L-AMINO ACIDS FROM α-KETO ACIDS

BACKGROUND OF THE INVENTION

The invention is directed to a method for the production of L-amino acids from α-ketocarboxylic acids by continuous fermentation with the aid of glutamate-producing bacteria in the presence of ammonium ions and of an energy supplier, especially glucose, with biomass retention.

L-amino acids can be obtained from α-keto acids by enzymatic conversion. Microbial conversion is also already known. Thus German OS 34 27 495 describes a method in which bacteria which excrete glutamate, especially bacteria of the genera Brevibacterium and Corynebacterium, are cultured in a culture medium within 6 to 40 hours, whereafter the α-ketocarboxylic acid to be transformed is added to the culture especially during the logarithmic growth phase (between approximately 20 and 72 hours) and is converted into L-amino acid.

According to another method described by the applicants (German patent application DE 34 19 585.8, the entire disclosure of which is hereby incorporated by reference), L-amino acids are likewise obtained by the microbial conversion of α-ketocarboxylic acids with the aid of glutamate-producing bacteria of the type named using growing or non-growing cells under aerobic conditions between 20° and 45° C. and a pH of 5-9 within 1-10 days. This method can be performed, as is indicated, continuously with retention of the biomass.

The microbial methods cited are relatively time consuming and the instant invention therefore has the task of improving the economy of the microbial conversion of α-keto acids into L-amino acids.

SUMMARY OF THE INVENTION

This task is solved by the method of the invention, which is essentially characterized in that the work is performed with a cell concentration in a fermenter of >30 g TS/l (TS is total solids), especially >60 g TS/l, suitably 60 g TS/l, residence times of 1-20 hours, especially 6-10 hours and with aeration and dispersion of air such that the L-lactate concentration of the product solution remains under 40 mmoles/l.

The cell concentration in the fermenter is preferably 80 to 120 grams TS/l, especially around 95 g TS/l. There is no need to supply a complex growth medium.

Biomass retention can be performed by microfiltration. Advantageously hollow fiber filters are employed for the microfiltration. The filter preferably has an average pore diameter of a maximum of 300 nm.

It is also possible to retain bacteria using a centrifugal disk separator in which case there is a discontinuous or constant removal of cells all of which are returned into the fermenter. In the case of discontinuous cell removal the operation is performed within 1 to 20 minutes for the total emptying using solid-discharging disk. The cell-poor runoff of the centrifugal separation can be microfiltered.

Preferably, there is employed a number of the genus Corynebacterium or Brevibacterium, especially a strain of *Corynebacterium glutamicum* or *Brevibacterium flavum* as the bacteria, most preferably *Corynebacterium glutamicum* ATCC 13032 or *Brevibacterium flavum* variant DM 40-3 (DSM 3812 derived from ATCC 14067).

The method of the invention is carried out with especially high cell concentrations and short residence times in a flow fermenter, whereby a limitation of nutrient and especially of oxygen is avoided at the same time.

While a partial removal of cell material with the product flow usually occurs in continuous methods with biomass retention in order to reduce the portions of old cells and cell fragments to a limited mass and to obtain a desired age distribution, a very extensive accumulation of cells is provided in accordance with the invention which is retained practically completely in the fermenter.

A sufficiently rapid return of the cell mass into the fermenter is naturally connected with the accumulation of the cell mass in the fermenter by filtration and/or separation. This return is achieved by a minimum volume flow in the external circuit which takes into account technical limitations such as pressure drop, foam formation, etc. and the oxygen requirement of the cells.

This extensive retention of the cells in the fermenter yields a practically cell-free product solution and such a high cell concentration in the fermenter that a growth limitation of the bacteria is given, whereby, however, a limitation of oxygen or nutrient is avoided.

A high selectivity of the L-amino acid formation is achieved under these conditions with a short residence time and a high conversion, i.e, high rate on yield. Selectivity is defined as the ratio of produce amino acid formed to the conversion of the precursor (keto acid).

This results in both an economic operation of the fermenter and also in a simplification of the work-up of the product solution, which can be additionally aided by the fact that according to a preferred embodiment, the work is performed without the supply of complex medium (such as yeast extract, beef extract, protein hydrolysate, etc.)

For the rest, the composition of the culture medium, its pH and the temperature correspond to the known method, whereby, however, the work is preferably performed without complex medium. The energy supplier can be glucose in particular, as is customary. Alternatively, it is of course possible to provide other energy suppliers such as sugar in general, acetate, etc. The presence of this energy supplier is necessary to make available sufficient amounts of reduction equivalents for the production of the L-amino acid and to assure the conservation metabolism. The energy supplier can no longer be completely utilized with a short residence time and limited cell growth, whereby the utilization of formed L-amino acid by the bacteria is then negligible in any case.

A sufficient oxygen supply is defined via the L-lactate concentration in the product solution: As is known, L-lactate is excreted by the bacteria if their oxygen supply is limited. Thus, one can deduce a sufficient or insufficient oxygen supply of the bacteria by measuring the L-lactate concentration in the product flow.

The following table shows examples for the work range of the invention:

| Operating point | 1 | 2 | 3 |
|---|---|---|---|
| Dry cell mass $\frac{g\ TS}{l}$ | 32.4 | 82.2 | 95.3 |
| Residence time [h] | 19.6 | 8.1 | 3.1 |

-continued

| Operating point | 1 | 2 | 3 |
|---|---|---|---|
| rate of yield $\frac{g}{l \times d}$ | 16.4 | 38.3 | 79.4 |
| Conversion [%] | 98.1 | 94.2 | 81.9 |
| Selectivity | 0.852 | 0.892 | 0.902 |
| Yield | 0.836 | 0.840 | 0.738 |

BRIEF DESCRIPTION OF THE DRAWING

The single FIGURE of the drawings is a graph which shows the selectivity and the yield of L-amino acid achieved over the range of ketocarboxylic acid conversions.

DETAILED DESCRIPTION

The test data refer to the production of L-leucine from α-ketoisocaproate with the aid of *Corynebacterium glutamicum* at pH 7.2; 30° C.; air throughput 0.16VVM; speed 600 rpms; $PO_2$—20% and redox voltage—OmV.

As is apparent from the test data, conversions over 90% can be achieved with residence times between approximately 6 and 10 hours and cell concentrations in the fermenter around 90 g TS/l in which conversions the selectivity still does not show any noticeable drop, as the graph shows.

Examples for the production of L-leucine and L-isoleucine in accordance with the invention are described below.

The process can comprise, consist essentially of or consist of the stated steps with the recited materials.

EXAMPLE 1

Production of L-leucine from α-ketoisocaproate and ammonium with *Corynebacterium glutamicum* (ATCC 13032) in a continuously operated fermentation with cell retention by filtration.

Product solution could be pumped out without cells at a constant filling volume of the fermenter by using two parallel-connected microfiltration tube bundle modules of the firm Enka, type "HA 11 24 H32". These filter modules have a membrane surface area of 0.05 square meters and a pore size of 300 nm.

The production medium contained 40 g/l glucose, 30 g/l ammonium sulfate, 20 g/l Na α-ketoisocaproate, 1 g/l potassium hydrogen phosphate, 0.25 g/l magnesium sulfate heptahydrate, 10 mg/l calcium chloride dihydrate, 10 mg/l iron sulfate heptahydrate, 7.6 mg/l manganese sulfate tetrahydrate, 0.4 mg/l biotin and 1 ml/l polypropylene glycol P1200 (firm—Roth). The pH was set at 7.2 with sodium hydroxide solution.

100 ml of a nutrient solution was inoculated with cells of Corynebacterium glutamicum (ATCC 13032) as initial culture in a 500 ml Erlenmeyer flask with 2 baffles. The nutrient solution contained 20 g/l glucose, 10 g/l Bacto-Peptone (Difco), 10 g/l yeast extract (Merck) and 2.5 g/l sodium chloride. The pH was set at 7.2 with sodium hydroxide solution. After 24 hours agitation at 100 rpms at 30° C., the cell suspension obtained was put into a 2 l Erlenmeyer flask with 2 baffles with 500 ml of a nutrient solution. This nutrient solution had the same composition as the production medium, only, 20 g/l calcium carbonate was used as buffer substance. Calcium chloride was not used. The pH of this nutrient solution was set at 7.2 before the addition of the calcium carbonate with sodium hydroxide solution. After 24 hours agitation at 100 rpms at 30° C., the cell suspension obtained was put into a fermenter as inoculum to 3 l production medium.

The nutrient solutions were autoclaved prior to usage 30 minutes at 121° C. and 1.1 bar vapor pressure. Glucose, α-ketoisocaproate and the residual constituents, except for calcium carbonate, were each autoclaved separately. Calcium carbonate was sterilized dry 8 hours at 150° C. After cooling, all nutrient media constituents were sterilely combined. The fermenter and the microfiltration module were sterilized with water 30 minutes at 121° C. and 1.1 bar vapor pressure. After the sterilization, the water used for moist sterilization was let out of the fermenter and the microfiltration module in a sterile manner and the fermenter was filled with 3 l production medium in a sterile manner.

1.8 days after inoculation of the fermenter, after the glucose present in the nutrient medium had been consumed and approximately 7 g dry cell mass/l of bacteria had grown, production medium started to be pumped in a sterile manner into the fermenter. At the same time, the same volumetric rate of flow of product solution was pumped without cells out of the fermenter. In order to separate the bacteria out of the product solution, from this time on, the content of the fermenter was constantly pumped with a gear pump at 250 l/h in a circuit through the interior of the hollow fiber filtration module. This current was intended to keep the formation of a coating of cells on the filtration surface as low as possible.

The fermentation was operated 3.5 days with a residence time of 7.2 hours, then 29 days with a residence times of 8.1 hours. The concentration of bacteria was held constant at approximately 35 g dry cell mass by periodic removal of solution containing cells. The cell growth was 6% per day on the average.

During the continuous operation of the fermentation, the conversion was between 85 and 95% at over 95% selectivity. Up to 15.5 g L-leucine/l was produced.

EXAMPLE 2

Production of L-leucine from α-ketoisocaproate and ammonium with *Corynebacterium glutamicum* (ATCC 13032) in a continuously operated fermentation with cell retention by filtration.

Product solution was pumped off without cells 5.8 days at a constant filling volume of the fermenter by using a microfiltration tube bundle module of the firm Enka, type "MD 080 TP 2N". The filtration membrane surface of the Enka module was 1 square meter and the pore size was 200 nm. A gear pump was used to feed the cell suspension in a circuit through the Enka module and the circuit volumetric rate of flow was approximately 300 l/h.

Prior to the start of the fermentation, the fermenter, the filtration system and the nutrient media were sterilized and filled with nutrient medium as described in Example 1. The composition of this production medium, as well as another 75 l for the continuous operation of the fermenter and the medium of the second and of the third initial culture differed from the previously described production medium in that 6% glucose and 4% ammonium sulfate were used instead of 4% and 3%. The rest of the composition was identical to that used otherwise. The second and third initial culture contained 2% calcium carbonate.

100 ml full complex with a pH of 7.4 and, in addition, 0.025% magnesium sulfate, along with the components described in Example 1, were inoculated with *Corynebacterium glutamicum* (ATCC 13032) as first initial culture and agitated 31 hours at 30° C. and 100 rpms. Then, 2 ml cell suspension was transferred as inoculation amount into a flask with 98 ml production medium. This second initial culture was agitated 89 hours at 30° C. and 100 rpms. Again, 2 ml cell suspension was transferred as inoculation amount into a flask with 98 ml production medium. This third initial culture was agitated 55 hours at 30° C. and 100 rpms and then completely used to inoculate the fermenter.

After the culturing phase was over and the glucose had been consumed, the fermenter was operated in a continuous manner as described in Example 1. The hollow fiber filter module was used 5.8 days for cell retention. At a residence time of 19.6 hours, a conversion of 98.1% was achieved at a selectivity of 85.2%, the L-leucine concentration was 13.4 g/l. At a residence times of 3.1 hours, the conversion was 81.9% at 90.2% selectivity. The L-leucine concentration was 10.4 g/l at a rate of yield of 79.4 g L-leucine per 1 reaction volume and day. The concentration of bacteria was at 19.6 hours residence times approximately 32 g dry cell mass per 1, at 3.1 hours residence times approximately 95 g dry cell mass per 1.

EXAMPLE 3

Production of L-isoleucine from α-ketobutyrate and ammonium with *Corynebacterium glutamicum* (ATCC 13032) in a continuously operated fermentation with cell retention by filtration.

Product solution was pumped off without cells at a constant filling volume of the fermenter by using a microfiltration tube bundle module of the firma Enka, type "MD 080 TP 2N". The filtration membrane surface of the Enka module was 1 square meter, the pore size 200 nm. A gear pump was used to feed the cell suspension in a circuit through the Enka module and the circuit volumetric rate of flow was approximately 300 l/h.

Prior to the start of the fermentation, the fermenter, the filtration devices and the nutrient media were sterilized and filled with nutrient medium as described in Example 1.

The production medium contained: 40 g/l glucose, 20 g/l ammonium sulfate, 20 g/l Na-α-ketobutyrate, 1 g/l potassium hydrogen phosphate, 1 g/l magnesium sulfate heptahydrate, 10 mg/l calcium chloride dihydrate, 10 mg/l iron sulfate heptahydrate, 7.6 mg/l manganese sulfate tetrahydrate, 0.4 mg/l biotin, 0.1 g/l L-valine, 0.1 g/l L-leucine and 1 ml/l polypropylene glycol P1200 (firm-Roth). The pH was set with sodium hydroxide solution at 7.4.

100 ml complex medium with a pH of 7.4 and, in addition, 0.025% magnesium sulfate along with the components described in Example 1 were inoculated with *Corynebacterium glutamicum* as first initial culture and agitated 23 hours at 30° C. and 100 rpms. Then, 60 ml cell suspension was put as inoculation amount into a flask with 600 ml production medium. This production medium contained 20 g/l glucose, 10 g/l Na-α-ketobutyrate instead of the above-named respective concentrations and additionally 20 g/l calcium carbonate.

This second initial culture was agitated 27 hours at 30° C. and 100 rpms and then completely used to inoculate the fermenter.

After the culturing phase was ended and the glucose had been consumed, the fermenter was operated in a continuous manner as described in Example 1. The hollow fiber filter module was used for 11 days for cell retention. After 4 days of continuous operation of the fermentation, the glucose concentration in the nutrient medium was raised to 60 g/l. During the fermentation, the pH was held constant at 7.4 by dosing sodium hydroxide solution. A limiting of oxygen could be avoided by an aeration, so that no appreciable amount of lactate was measured in the product solution.

At a residence time of 7 hours a conversion of 66% was achieved, at a selectivity of 54%, the L-isoleucine concentration was 5.5 g/l, at a rate of yield of 17.5 g L-isoleucine per 1 reaction volume and day. The concentration of bacteria was approximately 92 g dry cell mass per 1.

EXAMPLE 4

Production of L-isoleucine from α-ketobutyrate and ammonium with *Brevibacterium flavum* variant DM40-3 (DSM 3812) (German Microorganism Collection 3812) derived from ATCC 14067 in a continuously operated fermentation with cell retention by filtration.

Product solution was able to be pumped off without cells at a constant filling volume of the fermenter by using a microfiltration tube bundle module of the firm Enka, type "MD 080 TP 2N". The filtration membrane area of the Enka module was 1 square meter, the pore size was 200 nm. A gear pump was used to feed the cell suspension in a circuit through the Enka module, the circuit volumetric rate of flow was approximately 300 l/h.

Prior to the start of the fermentation, the fermenter, the filtration devices and a nutrient media container were sterilized as described in Example 1. The nutrient media components were added in a sterilely filtered manner with the exception of the trace elements. The trace elements were already contained in the water used to sterilize the nutrient media container.

The production medium contained: 100 g/l glucose, 20 g/l ammonium sulfate, 8 g/l α-ketobutyric acid, 1 g/l potassium hydrogen phosphate, 1 g/l magnesium sulfate heptahydrate, 10 mg/l calcium chloride dihydrate, 10 mg/l iron sulfate heptahydrate, 5 mg/l manganese sulfate tetrahydrate, 1 mg/l biotin and 1 ml/l polypropylene glycol P1200 (firm—Roth). The pH was set at 7.4 with sodium hydroxide solution.

100 ml of a medium with 30 g/l "Caso-Boullion" (Merck) which was set at pH 7.4 with sodium hydroxide solution was inoculated with *Brevibacterium flavum* variant DM40-3 (derived from ATCC 14067) as the first initial culture and agitated 16 hours at 30° C. and 100 rpms. Then, 60 ml cell suspension was put into a flask with 600 ml of the same medium as inoculation amount. This second initial culture was agitated 4 hours at 30° C. and 100 rpms and then completely used for inoculating the fermenter.

After the growth phase was ended and the glucose had been consumed, the fermenter was operated in a continuous manner as described in Example 1. The hollow fiber filter module was used 18 days for cell retention. During the fermentation, the pH was held constant at 7.4 by dosing sodium hydroxide solution.

At a dwell time of 5 hours, an L-isoleucine concentration of 2.5 g/l was achieved at a rate of yield of 13.5 g L-isoleucine per 1 reaction volume and day. The concentration of bacteria was approximately 80 g dry cell mass per 1.

It is claimed:

1. A method of producing an L-amino acid from an α-ketocarboxylic acid comprising continuous fermentation with the aid of glutamate-producing bacteria in the presence of ammonium ions and of an energy supplier, with biomass retention, wherein there is employed a cell concentration in the fermenter of >260 g.TS/l, dwell times of 1-20 hours, and with aeration and dispersal of air such that the L-lactate concentration of the product solution remains under 40 mmoles/l.

2. A method according to claim 1, wherein the energy supplier is glucose.

3. A method according to claim 1 wherein the cell concentration is 60 g TS/l and the residence time is 6-10 hours.

4. A method according to one of claims 1 to 3, characterized in that the biomass retention is performed by microfiltration.

5. A method according to claim 4, wherein the cell concentration in the fermenter is 80 to 120 g TS/l.

6. A method according to claim 5 wherein the cell concentration is around 95 g TS/l.

7. A method according to claim 1 which is carried out without supplying a complex medium.

8. A method according to claim 1 wherein hollow fiber filters are used for the microfiltration.

9. A method according to claim 8 characterized in that a filter with an average pore diameter of a maximum of 300 nm is used.

10. A method according to claim 1 comprising using a centrifugal disk separator for the retention of bacteria with a discontinuous or constant removal of cells which are all returned into the fermenter.

11. A method according to claim 10 comprising a microfiltration of the cell-poor runoff of the centrifugal separation.

12. A method according to claim 1 wherein there is used a representative of the genus Cornebacterium or Brevibacterium is used as bacterium.

13. A method according to claim 12 wherein there is used *Corynebacterium glutamicum* or *Brevibacterium flavum*.

14. A method according to claim 13 wherein there is used *Corynebacterium glutamicum* ATCC 13032 or *Brevibacterium flavum* variant DM 40-3 (DSM 3812).

* * * * *